United States Patent [19]

Ito et al.

[11] 4,036,217
[45] July 19, 1977

[54] DEVICE FOR MEASURING A RESPIRED AMOUNT OF AIR

[75] Inventors: Ayao Ito; Akinori Ishida, both of Yokohama, Japan

[73] Assignee: Tokyo Shibaura Electric Co., Ltd., Tokyo, Japan

[21] Appl. No.: 672,439

[22] Filed: Mar. 31, 1976

[30] Foreign Application Priority Data

Mar. 31, 1975   Japan ................................. 50-38959

[51] Int. Cl.² ............................................. A61B 5/08
[52] U.S. Cl. .............................. 128/2.08; 128/2.1 Z; 128/DIG. 29
[58] Field of Search ............ 128/2.1 Z, 2.08, DIG. 29

[56] References Cited

U.S. PATENT DOCUMENTS

| | | | |
|---|---|---|---|
| 3,608,542 | 9/1971 | Pacela et al. | 128/2.1 R |
| 3,677,261 | 7/1972 | Day | 128/2.1 Z |
| 3,962,917 | 6/1976 | Terada | 128/2.08 X |
| 3,976,052 | 8/1976 | Junginger et al. | 128/2.1 Z |

*Primary Examiner*—Kyle L. Howell
*Attorney, Agent, or Firm*—Finnegan, Henderson, Farabow & Garrett

[57] ABSTRACT

There is provided a device for measuring a respired amount of air comprising a hot wire anemometer for converting the variation in the amount of air respired from human lungs into an electrical signal, an integrator circuit for integrating an inhalation phase component of the output signal from the hot wire anemometer, and an impedance pneumograph for generating an output signal corresponding to the variation in the respired amount of air. The output signal from the integrator is stored in a memory in accordance with the output signal from the impedance pneumograph. The information signal stored in the memory is read out from the memory in accordance with an address signal corresponding to the amplitude of the output signal from the impedance pneumograph and is then displayed by a display.

20 Claims, 35 Drawing Figures

DEVICE FOR MEASURING A RESPIRED AMOUNT OF AIR

BACKGROUND OF THE INVENTION

This invention relates to a device for measuring a respired amount of air having an impedance pneumograph, and more particularly to a device for measuring a respired amount of air capable of automatically calibrating a measuring signal produced from the impedance pneumograph and indicating an amount of air respired.

An impedance pneumograph is a device for detecting by using a pair of electrodes fitted to the breast of a living body, for example a patient, the variation in the amount of air respired by the patient from the variation of the impedance between the electrodes occurring in accordance with the patient's respiration. Accordingly, in the case of measuring a respired amount of air by (a respired amount of air-measuring device having) an impedance pneumograph), it is necessary to first calibrate the output signal of the impedance pneumograph in accordance with the respired amount of air. Conventionally, this calibrating operation was manually carried out. That is, the calibrating operation of the device was performed by manually increasing or decreasing the amplitude of the output signal of the impedance pneumograph using as a reference the output signal of a respired amount of air-gauging instrument such as a hot wire anemometer capable of gauging the absolute value of the respired amount of air. Such manual calibrating operation, however, is complicated and requires much time. Since, during the calibrating operation, a sensing section of the hot wire anemometer is usually set in the patient's mouth, the prolongation of the calibrating time causes a higher load to be applied to the patient. Actually, since this type of device is operated by a doctor or nurse who is unfamiliar with the handling operation, very much time is required for calibration, which will extremely distress the patient. This type of device, therefore, has low practicability.

SUMMARY OF THE INVENTION

Accordingly, the object of the invention is to provide a device for measuring a respired amount of air automatically and permitting the calibration in a short time.

According to a preferred embodiment of the invention, there is provided a device for measuring a respired amount of air which comprises a signal generator for detecting an amount of air respired by a living body to be measured for generating an electrical signal corresponding to the respired amount of air, an impedance pneumograph for detecting the impedance variation occurring in accordance with the respiration of the living body, a reference level setting circuit connected to receive the output signal from the impedance pneumograph to set a reference level for the output signal of the impedance pneumograph, a memory circuit for receiving the output signal from the reference level setting circuit as a writing address signal and storing therein as an information signal that output signal from the signal generator which corresponds to the output signal from the reference level setting circuit, a peak-to-peak amplitude detector for detecting a maximum amplitude within each cycle of the output signal from the impedance pneumograph, a level detector for detecting that the output signal from the respired amount of air-indicating signal generator has exceeded a specified level, and a circuit for, upon receipt of the output signal from the level detector, electrically isolating the respired amount of air-indicating signal generator and reference level setting circuit from the memory circuit and simultaneously coupling the peak-to-peak amplitude detector to the memory circuit to read out a respired amount of air-indicating information signal stored in the memory circuit by using the output signal from the peak-to-peak amplitude detector as a reading address signal.

DETAILED DESCRIPTION OF THE PREFERRED EMBODIMENTS

A device for measuring a respired amount of air according to an embodiment of the invention is now explained with reference to the accompanying drawings.

Figure 1A:
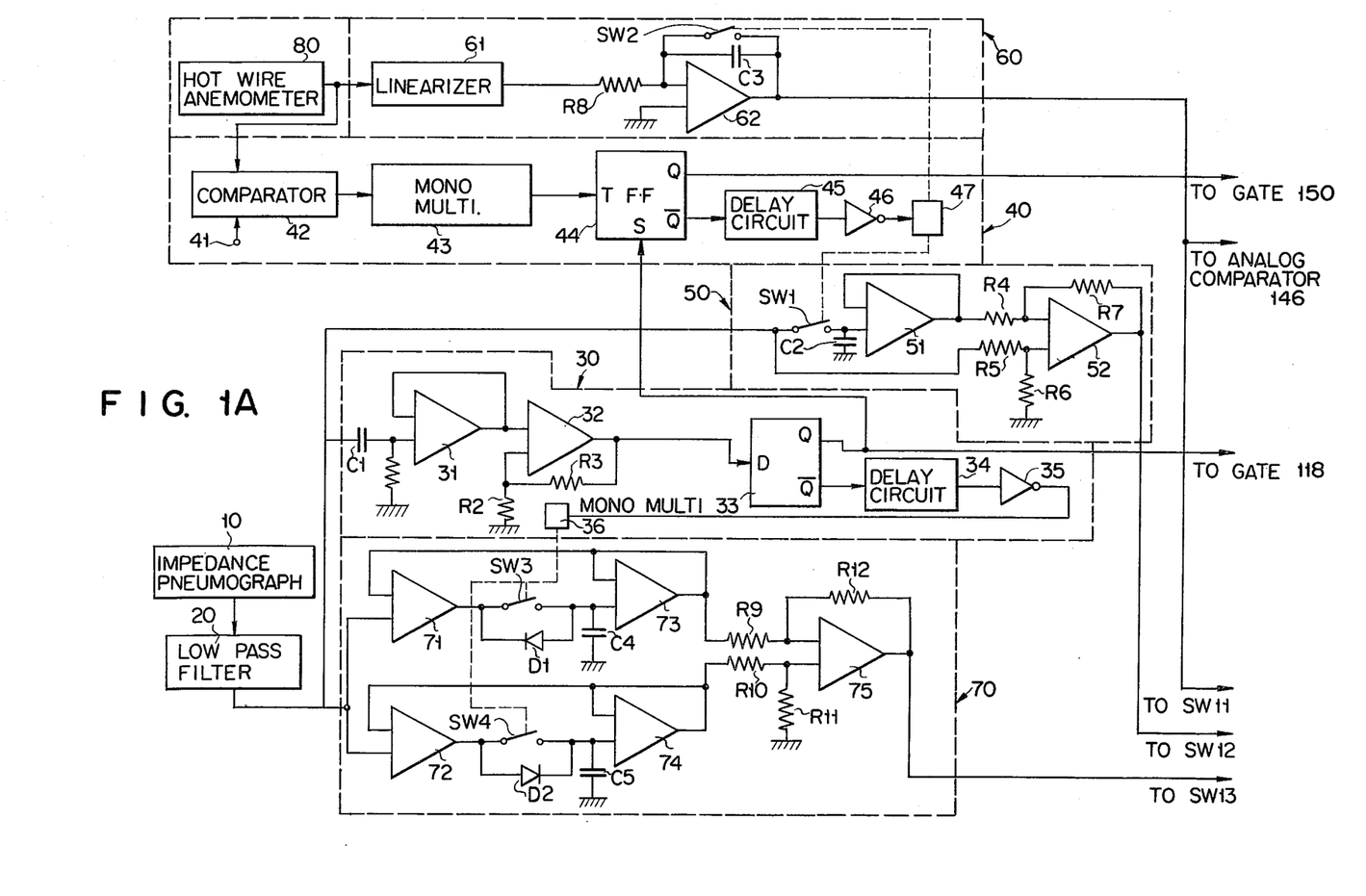
FIGS. 1A and 1B are circuit diagrams showing a device for measuring a respired amount of air according to an embodiment of the invention.
Figure 1B:
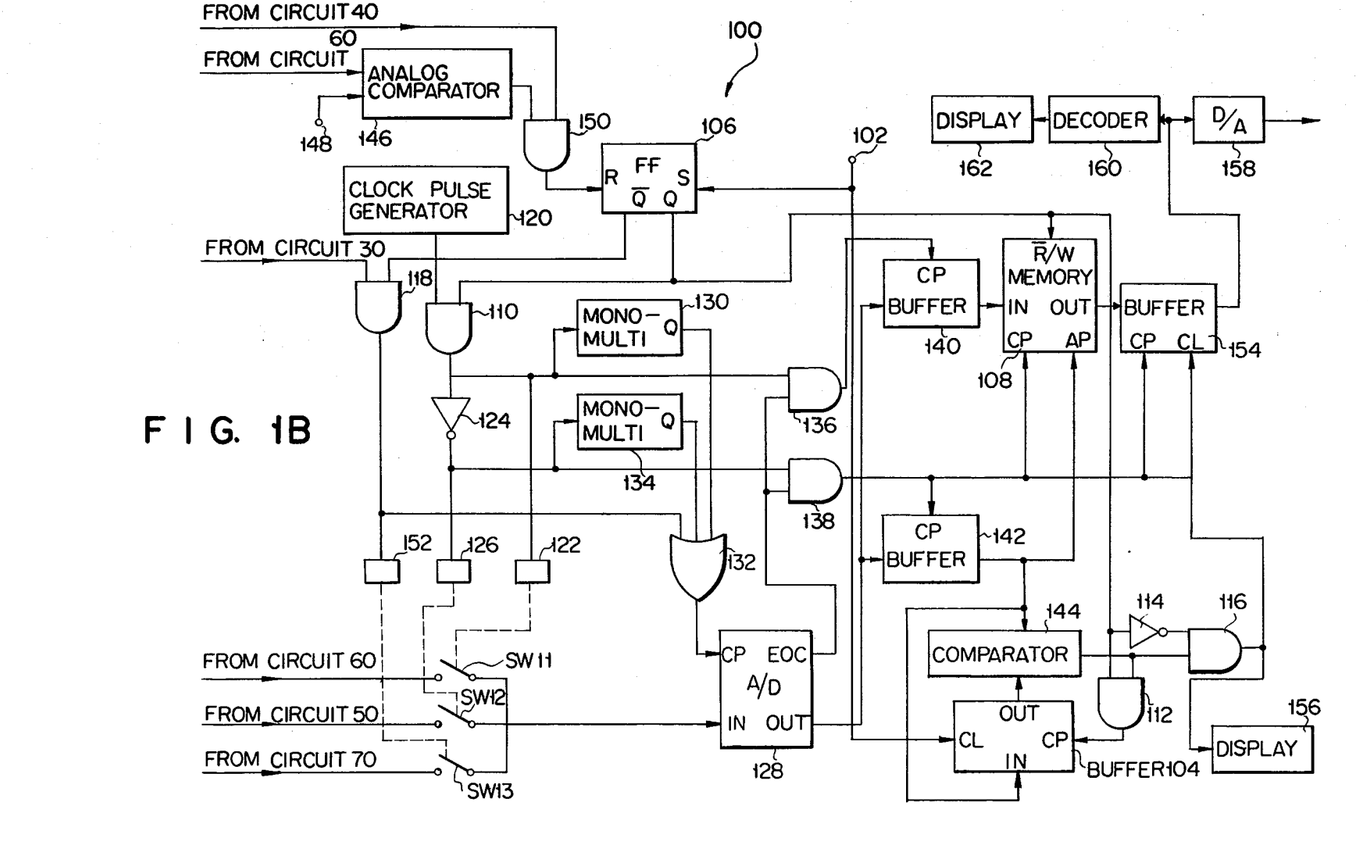

FIGS. 1A to 1B show that circuit of the device which is designed to generate various signals required to measure a respired amount of air and a calibration and measurement-control circuit of the device, respectively. An impedance pheumograph 10 shown in FIG. 1A is designed to detect that impedance of a patient between a pair of electrodes fitted to the patient's breast which varies with the respiration of the patient and to generate an electrical signal denoting this variation in impedance. A low-pass filter 20 receives the output signal from the impedance pneumograph 10 and removes a high frequency component of this output signal to permit the passage therethrough of only a low frequency component. The output signal from the filter 20 is supplied to a respiration phase detecting circuit 30, a reference level setting circuit 50 and a peak-to-peak amplitude detector 70.

Figure 2:
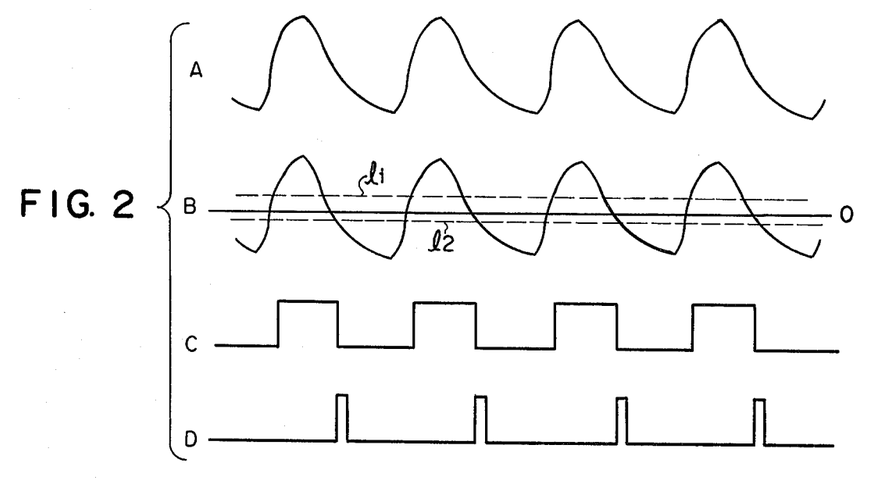
FIGS. 2A to 2D are waveforms of the output signals from individual sections of a respiration phase detecting circuit used in the device shown in FIG. 1.

The respiration phase detecting circuit 30 is a circuit which receives such an output signal from the low-pass filter 20 as shown in FIG. 2A to generate an exhalation phase pulse synchronized with an exhalation phase of said output signal. The output signal from the low-pass filter 20 is applied to an operational amplifier 31 through a capacitor C1 of the respiration phase detecting circuit 30. From the amplifier 31 is generated an output signal prepared by removing a DC component from the output signal of the filter 20 as shown in FIG. 2B. The output signal from the amplifier 31 is applied to a comparator composed of resistors R2, R3 and operational amplifier 32 and having hysteresis characteristics. From the amplifier 32 is generated a pulse which, as shown in FIGS. 2B and 2C, rises when the level of the output signal from the amplifier 31 is $l_1$ in the inhalation, and falls when the level is $l_2$ in the exhalation. Upon receipt of this pulse at its input terminal D, a monostable multivibrator 33 generates such a pulse having a small pulse width as shown in FIG. 2D from its output terminal Q. In this manner, a pulse synchronized with the exhalation phase is obtained from the respiration phase detecting circuit 30. On the other hand, the output signal from an output terminal $\overline{Q}$ of the multivibrator 33 is slightly delayed by a delay circuit 34, inverted by an inverter 35 and then applied to a switch driving section 36.

Figure 3:
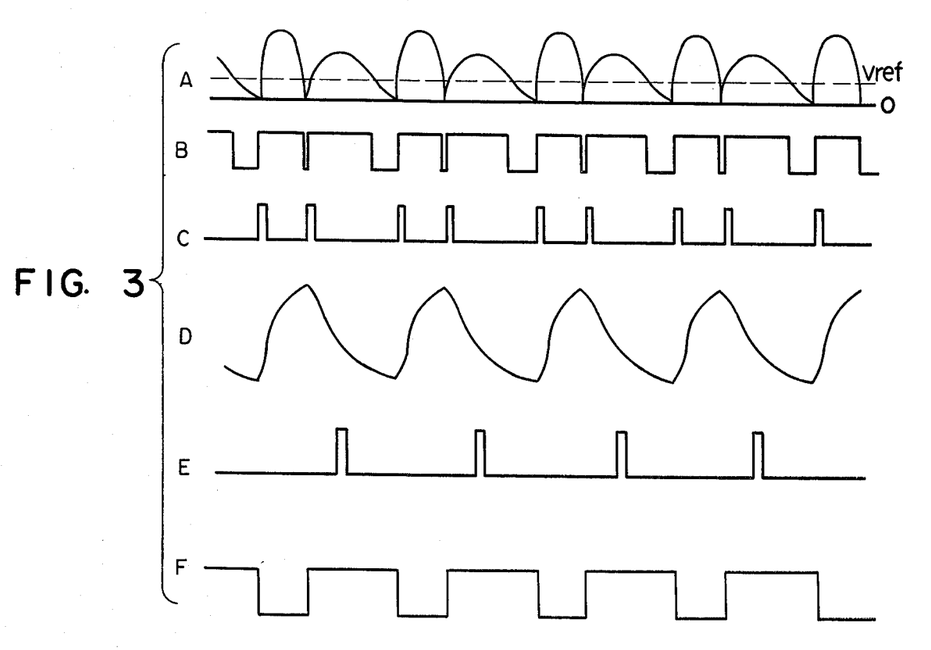
FIGS. 3A to 3F are waveforms of the output signals from individual sections of a respiration phase descriminating circuit used in the device shown in FIG. 1.

A respiration phase discriminating circuit 40 is a circuit which receives the output signal from a hot wire anemometer 80 to discriminate the exhalation phase of this output signal from the inhalation phase thereof. The hot wire anemometer 80 generates an electrical signal corresponding to the flow speed of inhaled and exhaled air as shown in FIG. 3A. A comparator 42 compares the output signal from the hot wire anemometer 80 with a reference voltage signal Vref applied to a reference voltage terminal 41 to generate a binary level signal which, as shown in FIG. 3B, when the level of said output signal is lower than the level of the reference voltage signal Vref, has a low level and when the former is higher than the latter, has a high level. The output signal from the comparator 42 is applied to a monostable multivibrator 43 and, when rising, energizes the monostable multivibrator 43 to cause it to generate such a pulse having a small pulse width as shown in FIG. 3C. This pulse signal is applied to a trigger terminal T of an R-S-T flip-flop circuit 44. The flip-flop circuit 44 receives at its set terminal S the output signal shown in FIG. 3E from the exhalation phase detecting circuit 30, that is, a pulse signal generated within the exhalation phase period of the output signal shown in FIG. 3D from the impedance pneumograph 10. Thus, upon receipt of the output pulse from the respiration phase detecting circuit 30, the flip-flop circuit 44 is set within the exhalation phase period of the output signal from the impedance pneumograph 10 and simultaneously generates from its output terminal Q the signal having a rectangular waveform shown in FIG. 3F which is inverted each time the circuit 44 receives the output pulse from the monostable multivibrator 43 at its trigger terminal T. That is to say, the flip-flop circuit 44 is set within the exhalation phase period of the output signal from the hot wire anemometer 80 and reset within the inhalation phase period thereof. The output signal from the output terminal $\overline{Q}$ of the flip-flop circuit 44 is delayed a small length of time by a delay circuit 45, inverted by an inverter 46 and then applied to a switch driving section 47.

Figure 4:
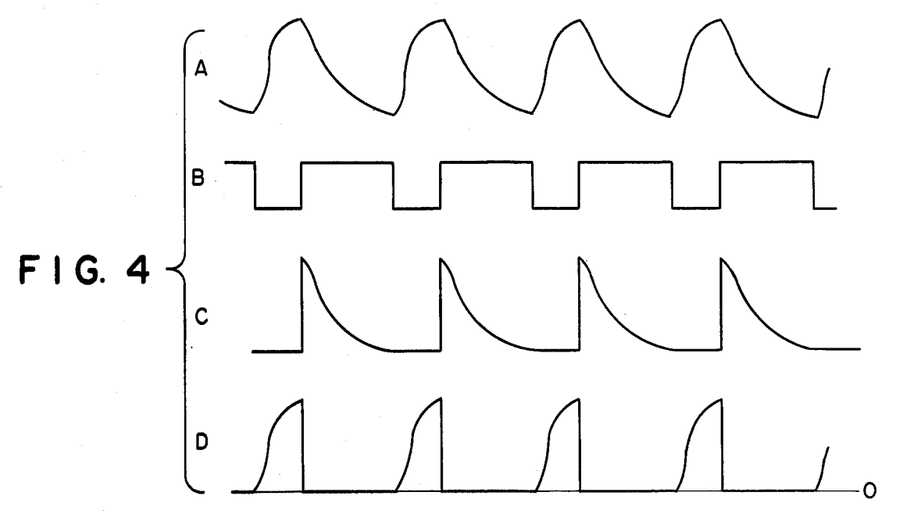
FIGS. 4A to 4D are waveforms of the output signals from individual sections of a reference level setting circuit used in the device shown in FIG. 1.

A reference level setting circuit 50 is a circuit which sets to zero level that potential of the output signal from the impedance pneumograph 10 which appears at the point of time at which the inhalation commences. A switch SW1 of the circuit 50 is operated by the switch driving section 47 in accordance with the output signal shown in FIG. 4B from the inverter 46 of the respiration phase discriminating circuit 40. The output signal from the inverter 46 may be substantially identified with the output signal from the output terminal Q of the flip-flop circuit 44 although delayed a small length of time by the delay circuit 45. Accordingly, the switch SW1 is closed during the exhalation phase period of the output signal from the hot wire anemometer 80, namely, during the high level period of the signal shown in FIG. 4B, and opened during the inhalation phase period of said output signal, namely, during the low level period of the signal shown in FIG. 4B. A sample holding circuit composed of the switch SW1, capacitor C2 and operation amplifier 51 receives the signal shown in FIG. 4A sent over from the impedance pneumograph 10 to generate such an output signal as shown in FIG. 4C. That is to say, the output signal from the operation amplifier 51 is maintained at a specified level while the switch SW1 is opened, and has the same level as that of the signal shown in FIG. 4A while the switch SW1 is closed. A subtracting circuit composed of resistors R4, R5, R6 and R7 and an operation amplifier 52 receives the output signals from the operation amplifier 51 and impedance pneumograph 10 to determine the difference between the output signals and generates such an output signal as shown in FIG. 4D. This output signal is a one prepared by setting to zero level those potentials of the output signal from the impedance pneumograph 10 which appear at a point of inhalation phase-starting time and in the exhalation phase period of that output signal.

Figure 5:
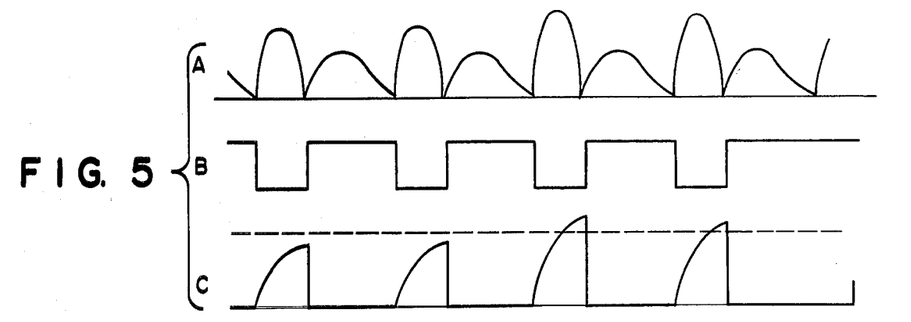
FIGS. 5A to 5C are waveforms of the output signals from individual sections of an inhalation phase component integrator circuit used in the device shown in FIG. 1.
Figure 6:
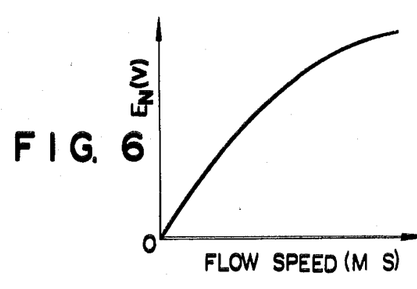
FIGS. 6 and 7 are respective input-output characteristic curve diagrams of a hot wire anemometer and linearizer used in the device shown in FIG. 1.
Figure 7:
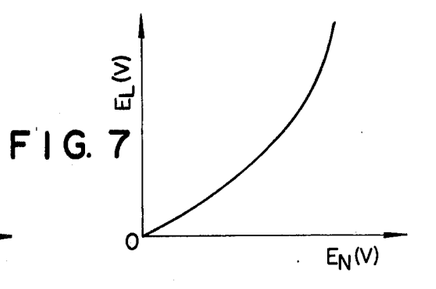

An inhalation phase component integrator circuit 60 is a circuit which receives the output signal from the hot wire anemometer 80, linearizes this output signal and thereafter integrates only a single component corresponding to the inhalation phase period of that output signal. The relationship between the output signal $E_N$ from the hot wire anemometer 80 shown in, for example, FIG. 3A and the flow speed of air respired is represented by the curve shown in FIG. 6 and indicates no linear pattern. In order to obtain a signal $E_L$ linearly varying with respect to the variation in the flow speed of air respired, the output signal $E_N$ from the hot wire anemometer 80 is applied to a linearizer 61 having such input and output characteristics as shown in FIG. 7. The output signal shown in FIG. 5A, thus obtained from the linearizer 61 and presenting a linear variation with respect to the flow speed of air respired, is applied to an integrator composed of a resistor R8, capacitor C3 and operation amplifier 62. A switch SW2 coupled in parallel to the capacitor C3 is so driven by a switch driving section 47 so as to be opened during the inhalation phase period of the output signal from the hot wire anemometer and closed during the exhalation phase period thereof, the switch driving section 47 being energized upon receipt of the output signal from the inverter 46 which is shown in FIG. 5B. Thus, from the operational amplifier 62 is obtained the integrated signal shown in FIG. 5C which is prepared by integrating only a signal component corresponding to the inhalation phase period of the input signal to the integrator.

Figure 8:
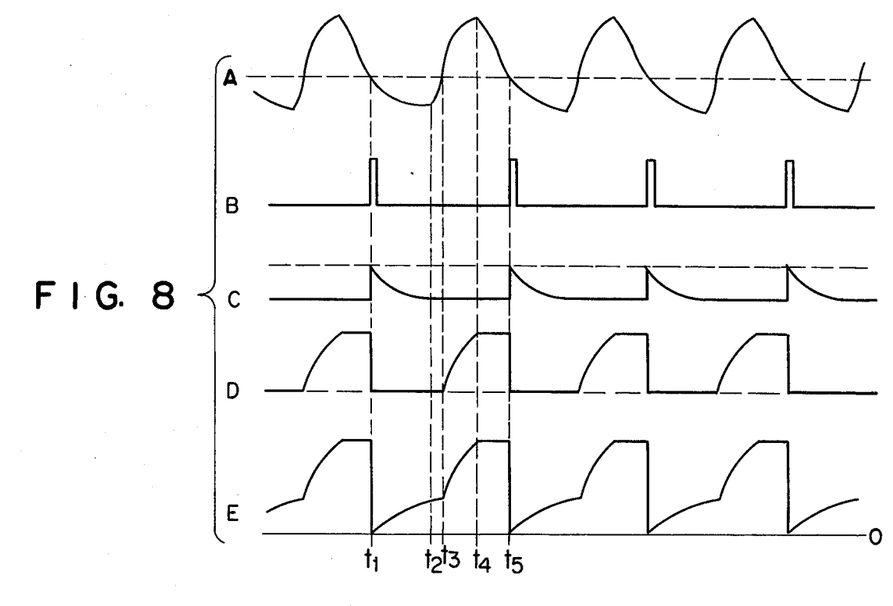
FIGS. 8A to 8E are waveforms of the output signals from individual sections of a peak-to-peak amplitude detector used in the device shown in FIG. 1.

A peak-to-peak amplitude detector 70 is a circuit which detects a maximum amplitude in each respiration phase period of the output signal generated from the impedance pneumograph 10. Switches SW3 and SW4 of the detector 70 are driven by a switch driving section 36 energized upon receipt of that output signal from the inverter 35 which is shown in FIG. 8B. The output signal from the inverter 35 may be substantially identified with the output signal from the output terminal Q of the monostable multivibrator 33 although delayed a small length of time by the delay circuit 34.

When, at a point of time $t_1$, the switch driving section 36 is energized by the pulse signal generated from the inverter 35, the switch SW3 is closed for an infinitesimal time, whereby the voltage level of a capacitor C4, i.e., the input voltage level to an operation amplifier 73 becomes equal to a voltage level corresponding to the level of the respiration signal shown in FIG. 8A which is generated from the impedance pneumograph 10 at the point of time $t_1$. Thereafter, when the switch SW3 is opened, the capacitor C4 is discharged through a diode D1, and at a point of time $t_2$ finishes being discharged, whereby the detector 70 detects a minimum amplitude of the respiration signal from the impedance pneumograph 10. The voltage level of the capacitor C4 is kept unchanged until the switch SW1 is next closed at a point of time $t_5$. That is, the operation amplifier 73 generates such an output signal as shown in FIG. 8C. On the other hand, when, at a point of time $t_1$, the switch SW4 is closed by the switch driving section 36, the voltage level of a capacitor C5, i.e., the input voltage level to an operation amplifier 74 instantaneously becomes equal to a voltage level corresponding to the level of the respiration signal (FIG. 8A) generated from the impedance pneumograph 10 at the point of time $t_1$. Thereafter, when the switch SW4 is opened, the voltage level of the capacitor C5 is kept unchanged until a point of time $t_3$ is reached, namely, until the respiration signal becomes equal to the level this signal has displaced at the point of time $t_1$. Thereafter, the capacitor C5 is gradually charged until a point of time $t_4$ is reached at which the respiration signal has a maximum amplitude. This condition is maintained until a point of time $t_5$ is reached at which the switch SW4 is closed. Thus, the operation amplifier 74 generates such an output signal as shown in FIG. 8D. The output signals from the operation amplifiers 73, 74 are applied to a subtracting circuit composed of resistors R9, R10, R11 and R12 and operation amplifier 75. The output signal from the subtracting circuit, i.e., the output signal from the operation amplifier 75 is a one obtained by subtracting the output signal of the operation amplifier 73 from the output signal of the operation amplifier 74 and, as shown in FIG. 8E, the lowest level of said output signal from the subtracting circuit is in coincidence with the zero level. From the signal shown in FIG. 8E is obtained a peak-to-peak amplitude of the respiration signal from the impedance pneumograph 10 in each respiration phase period.

Note that the operational amplifiers 71, 72 provided at the initial stage of the peak-to-peak detector 70 are used for purpose of minimizing the effect of a forward voltage drop across the diodes.

An automatic calibrating and measuring operation control circuit 100 is intended to receive the output signals from the circuits 50 and 60 to calibrate the output signal from the impedance pneumograph 10 using the output signal from the hot wire anemometer and, after performing the calibrating operation, carry out the respired amount of air-measuring operation using the output signal from the detector 70.

When a starting pulse is applied to a terminal 102, a largest-address buffer register 104 is cleared and simultaneously the flip-flop 106 is set, whereby the circuit 100 is set to a calibrating mode. When the flip-flop 106 is set, it generates at its output terminal Q an output signal having a high level. This output signal is applied to a read-write terminal $\overline{R/W}$ of a memory 108 to cause it to be brought to a write mode, and simultaneously is applied to AND gates 110 and 112 to open them. Further, the output signal from the output terminal Q of the flip-flop 106 is applied also to an AND gate 116 through an inverter 114 to close it. On the other hand, the output signal from an output terminal $\overline{Q}$ of the flip-flop 106 is applied to an AND gate 118 to close it.

When the AND gate 110 is opened, the clock pulse from a clock pulse generator 120 for generating a clock pulse of, for example, 10 kHz is supplied to a switch driving section 122 through the AND gate 110 and supplied also to a switch driving section 126 through an inverter 124. That is, the switch driving sections 122 and 126 are alternatively energized, and switches SW11 and SW12 are driven, respectively, by the switch driving sections 122 and 126 to be opened or closed. The output signals from the inhalation phase component integrator circuit 60 and reference level setting circuit 50 are alternately applied to an input terminal of an analog-digital converter 128 through the switches SW1 and SW2, respectively. A monostable multivibrator 130 receives the clock pulse from the AND gate 110 and, upon rise of this clock pulse, supplies a pulse signal having a small pulse width to an OR gate 132. A monostable multivibrator 134 receives the clock pulse from the inverter 124 and, upon rise of this clock pulse, supplies a pulse signal having a small pulse width to the OR gate 132. The output pulse from the OR gate 132 is applied to a clock terminal CP of the A/D converter 128 to cause it to effect the analog-digital converting operation. The converter 128 supplies a pulse signal denoting the completion of the A/D conversion to AND gates 136 and 138 each time the A/D converting time elapses after the A/D conversion commences, in other words, during a period converting from the point of time at which the converter 128 receives one pulse from the OR gate 132 to the point of time at which the converter 128 receives the next pulse from the OR gate 132. The AND gates 136 and 138 receive the output signals from the AND gate 110 and inverter 124, respectively, at the other input terminals. The pulse signals from the AND gates 136 and 138 are supplied to the respective clock terminals CP of an input buffer register 140 and an address buffer register 142 which are designed to receive also the output signal from the A/D converter 128. The address signal of the input buffer register 140 is written in the address position of the memory 108 corresponding to the output signal from the buffer register 142, in accordance with the output pulse signal produced from the AND gate 138 to a clock terminal CP of the memory 108. At this time, the output pulse signal from the address buffer register 142 is applied to a digital comparator 144 designed to receive the output signal from the largest-address buffer register 104, and comparison between the output signals is performed by the digital comparator 144. Where the level of the output signal from the address buffer register 142 is larger than that of the output signal from the largest-address buffer register 104, the output signal from the digital comparator 144 is applied to a clock terminal CP of the largest-address buffer register 104 through the AND gate 112 to write the address signal from the address buffer register 142 into the largest-address buffer register 104 as the largest address value.

The above-mentioned calibrating operation is completed when the output signal from the inhalation signal component integrator circuit 60 has exceeded a specified level, i.e., a level corresponding to an inhaled air amount of, for example, 0.8*l* and simultaneously the output signal from the respiration phase discriminating circuit 40 has shifted from the inhalation to the exhalation phase. The output signal from the inhalation signal component integrator circuit 60 is applied to one terminal of an analog comparator 146, which compares this input signal with a reference voltage applied to the other terminal of the comparator 146. When the level of the output signal from the circuit 60 has become higher than that of the reference voltage, the comparator 146 generates an output signal having a specified level for a specified period of time to open an AND gate 150. At this time, when the output signal from the respiration phase discriminating circuit 40 shifts from the inhalation to the exhalation phase, it is applied to a reset terminal R of the flip-flop circuit 106 through the AND gate 150 to reset the circuit 106, whereby the calibrating mode of the circuit 100 is changed over to the measuring mode.

When the R-S flip-flop circuit 106 is brought to a reset condition, the AND gate 110 is closed and the AND gate 118 is opened. Simultaneously, the signal applied to the read-write terminal R/W of the memory 108 from the output terminal Q of the flip-flop 106 has a low level, whereby the memory 108 is brought to a readout mode. Further, the output signal from the output terminal Q of the flip-flop 106 is applied to the AND gate 116 through the inverter 114 to open it. When the AND gate 118 is opened, the output pulse signal from the respiration phase detecting circuit 30 is applied to a switch driving section 152 through the AND gate 118. For this reason, a switch SW13 is closed for an infinitesimal time within the exhalation phase period of the respiration signal from the impedance pneumograph 10. As a result, the output signal from the peak-to-peak amplitude detector 70 is applied to the input terminal of the A/D converter 128 through the switch SW13. Further, the output pulse signal from the AND gate 118 is supplied to the clock terminal CP of the A/D converter 128 through the OR gate 132 to cause it to convert the output signal from the detector 70 into a digital signal. During a period covering from the point of time at which the output pulse signal from the AND gate 118 is applied to the clock terminal CP of the A/D converter 128 to the point of time at which the next pulse signal from the AND gate 118 is applied thereto, the converter 128 generates an output signal from its EOC terminal and this signal is applied to the AND gates 136 and 138. Since, during the measuring operation, the AND gate 136 is closed and the AND gate 138 is opened, the output pulse signal from the EOC terminal of the converter 128 is applied to the clock terminal CP of the address buffer register 142 through the AND gate 138. As a result, the output signal from the A/D converter 128 is stored in the buffer register 142. The output signal from the buffer register 142 is applied to an address terminal of the memory 108, whereby the content in the address position designated by the output signal from the buffer register 142 is read out by the output pulse signal from the AND gate 138. The content read out from the memory 108 is transferred into an output buffer register 154. On the other hand, the address value stored in the address buffer register 142 is compared with the address value stored in the largest-address buffer register 104 by the comparator 144.

Where, as a result of this comparison, the former address is greater than the latter address value, the output signal from the comparator 144 is applied to a clear terminal CL of the output buffer register 154 through the AND gate 116 to clear the content thereof, and simultaneously applied to an overrange, display device 156 to indicate that the address signal from the buffer register 142 is excessive. Where the address signal from the buffer register 142 is smaller than the address signal from the largest-address buffer register 104, the content of the output buffer register 154 is drawn out into an external circuit through a digital-analog converter 158, and simultaneously decoded by a decoder 160 and thereafter displayed by an output display device 162.

Since the above-explained device for measuring a respired amount of air is so designed that where the output signal of the inhalation phase component integrator circuit 60 remains lower than a specified level, the effective calibrating operation can not be performed. When the effective calibration operation is performed, the calibrated content is stored in the memory and the calibrating operation mode is changed over to the measuring operation mode, and thus the respired amount of air can be measured from the output signal of the impedance pneumograph. Since this respired amount of air as measured is displayed by the display device, the patient is freed from the application of an unnecessary load.

This invention has above been explained by describing one embodiment, but is not limited thereto. For instance, the foregoing embodiment referred to the case where the respired amount of air was measured by processing the signal corresponding to an inhaled amount of air, but, according to the invention, it is also possible to measure the respired amount of air through processing the signal corresponding to an exhaled amount of air by properly altering the circuits involved.

Figure 9:
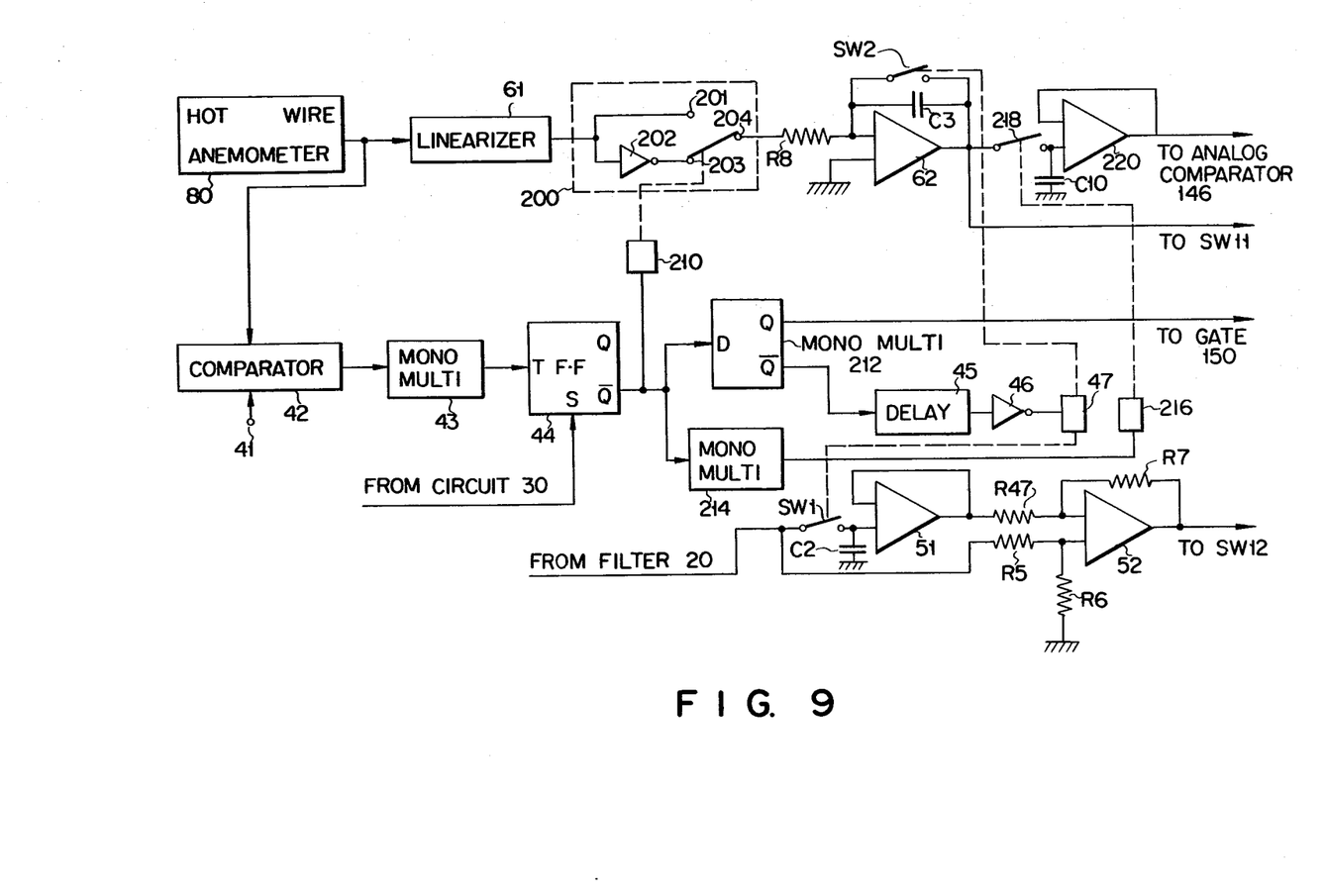
FIG. 9 is a block circuit diagram showing part of a device for measuring a respired amount of air according to another embodiment of the invention.

In FIG. 9, the same parts and sections as those of FIG. 1A are denoted by the same reference numerals, and detailed description thereof is omitted.

Figure 10:
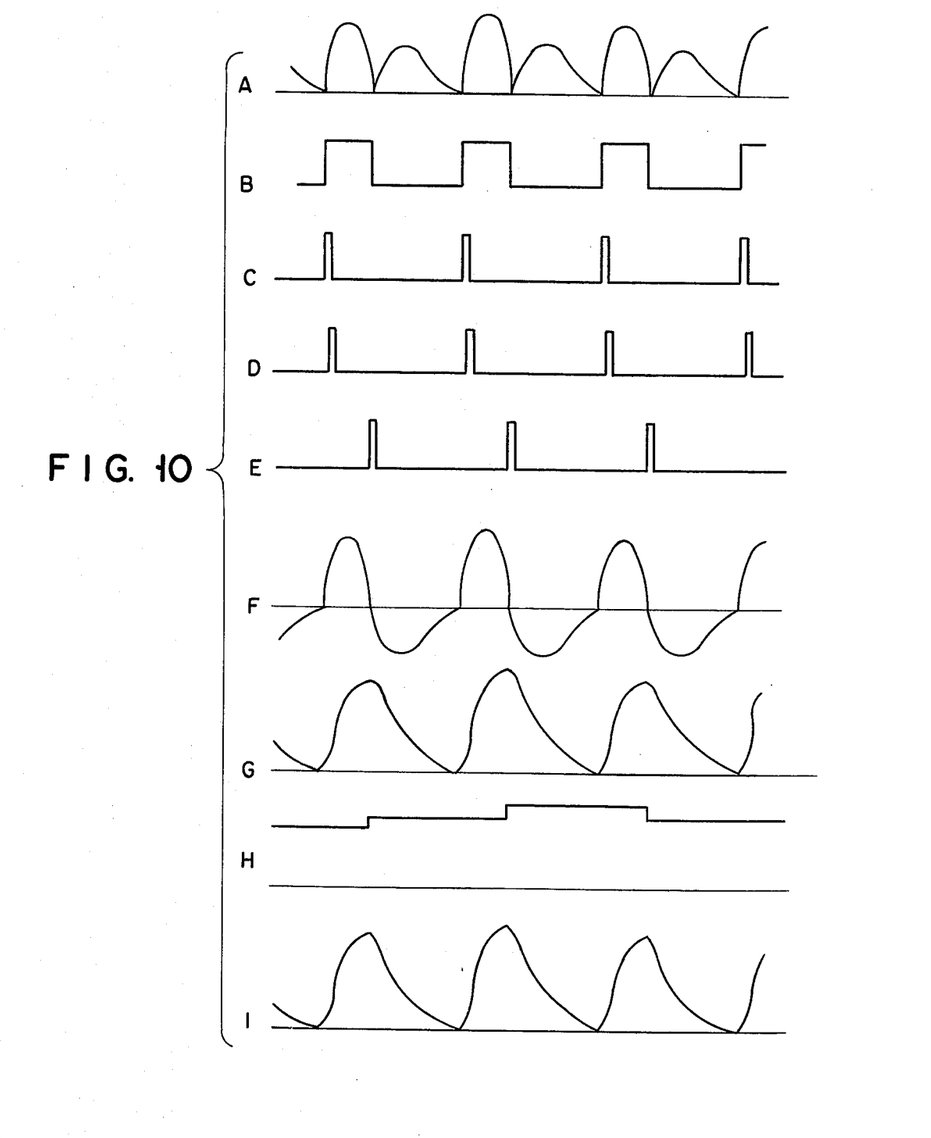
FIGS. 10A to 10I are waveforms of the output signals from individual sections of the device shown in FIG. 9.

The signal shown in FIG. 10B which is generated from the output terminal $\overline{Q}$ of the flip-flop circuit 44 is supplied to monostable multivibrators 212 and 214. The monostable multivibrator 212, upon the rise of the output pulse from the output terminal $\overline{Q}$ of the flip-flop circuit 44, generates a pulse having a small pulse width as shown in FIG. 10C from its output terminal Q. The output signal from the output terminal $\overline{Q}$ of the monostable multivibrator 212 is delayed a small period of time by the delay circuit 45 and then inverted by the inverter 46 to become such a signal as shown in FIG. 10D, and the signal is applied to the switch driving section 47. The monostable multivibrator 214, upon the fall of the output pulse from the output terminal $\overline{Q}$ of the flip-flop circuit 44, generates a pulse having a small pulse width as shown in FIG. 10E to energize a switch driving section 216.

The output signal from the linearizer C1 which is shown in FIG. 10A is supplied to a switching circuit 200. This switching circuit 200 is composed of a fixed contact 201 coupled to the output terminal of the linearizer 61, another fixed contact 203 coupled to the output terminal of the linearizer through an inverter 202, and a movable contact 204. This movable contact 204 is driven by a switch driving section 210 to be alternately coupled to the contact 201 or 203, whereby the switching circuit 200 inverts only the exhalation phase component of the input signal shown in FIG. 10A to generate an output signal shown in FIG. 10F. The output signal from the switching circuit 200 is supplied to the integrator composed of the resistor R8, capacitor C3 and operation amplifier 62. This integrator is provided with the switch SW2 coupled in parallel to the capacitor C3 and driven by the switch driving section 47. Through the operation of the switch SW2, the signal integrated by said integrator is made to have zero level at each cycle of respiration as shown in FIG. 10G. This integrated signal is applied to a holding circuit composed of a capacitor C10 and operational amplifier 220, through a switch 218 driven by the switch drving section 216. The output signal from the operation amplifier 220, as shown in FIG. 10H, has its level shifted to the level corresponding to a maximum output level of the operation amplifier 62 each time the switch 218 is closed and is maintained to have this shifted level until the switch 218 is next closed.

The switch SW1 of the reference level setting circuit 50 is driven by the switch driving section 47 energized by an output pulse having a small pulse width as shown in FIG. 10D. Therefore, this circuit 50 generates the output signal shown in FIG. 10I which is prepared by setting to zero level the lowest level of the output signal from the impedance pneumograph 10.

Note, in this case, that, for the purpose of permitting the flip-flop circuit 44 to be set within the inhalation phase period of the output signal from the impedance pneumograph 10, the monostable multivibrator 33 is so constructed as to generate an output pulse having a small pulse width upon the rise of the output pulse of the operation amplifier 32.

As above described, through permitting the operation amplifiier 62 to generate such a respired amount of air-indicating signal as shown in FIG. 10G instead of such an inhaled amount of air-indicating signal as shown in FIG. 5C and simultaneously permitting the operation amplifier 52 to generate such a signal corresponding to respired amount of air as shown in FIG. 10I instead of such a signal corresponding to an inhaled amount of air as shown in FIG. 4D, it is possible to measure the respired amount of air in accordance with the exhaled amount of air.

What we claim is:

1. A device for measuring a respired amount of air comprising a respired amount of air-indicating signal generator for detecting an amount of air respired by a body to be measured and generating an electrical signal corresponding to said respired amount of air, an impedance pneumograph for detecting an impedance variation corresponding to said respired amount of air of said body, a reference level setting circuit for receiving an output signal from said impedance pneumograph to set a reference level with respect to said output signal, a memory circuit for receiving, when it is placed in a write-in mode, an output signal from said reference level setting circuit as a writing address signal and storing as information an output signal from said respired amount of air-indicating signal generator corresponding to said output signal from said reference level setting circuit, a peak-to-peak amplitude detector for detecting a maximum amplitude for each cycle of said output signal from said impedance pneumograph, a calibration completion-detecting circuit for detecting that said output signal from said respired amount of air-indicating signal generator has exceeded a specified level, to indicate that a desired calibration signal has been obtained, and an operation mode selecting means for setting, when it has received a calibration completion-indicating output signal from said detecting circuit, said memory circuit to a readout mode and electrically isolating said respired amount of air-indicating signal generator and said reference level setting circuit from said memory circuit and simultaneously coupling said peak-to-peak amplitude detector to said memory circuit, thereby to read out a respired amount of air-indicating information signal stored in said memory circuit by using an output signal from said peak-to-peak amplitude detector as a reading address signal.

2. A device according to claim 1, which further comprises a display means for displaying output information read out from said memory circuit.

3. A device according to claim 1, wherein said respired amount of air-indicating signal generator includes a hot wire anemometer and an integrator circuit for integrating an output signal from said hot wire anemometer to supply an output signal to said calibration completion-detecting circuit.

4. A device according to claim 3, wherein said respired amount of air-indicating signal generator further includes a linearizer connected between said hot wire anemometer and said integrator circuit to generate an output signal linearly varying with respect to an amount of air respired by said body.

5. A device according to claim 3, wherein said calibration completion-detecting circuit includes a pulse generator connected to said hot wire anemometer to detect inhalation and exhalation phases of a respiration signal from said hot wire anemometer thereby to generate a pulse upon commencement of an inhalation phase period of said respiration signal, a level detector for detecting that the level of an output signal from said integrator circuit has exceeded a specified level, and a first logic circuit for receiving output signals from said level detector and said pulse generator to generate a pulse upon commencement of an inhalation phase period of the respiration signal generated from said hot wire anemometer after said level of an output signal from said integrator circuit has exceeded said specified level.

6. A device according to claim 1, wherein said operation mode selecting means includes a flip-flop circuit for receiving said calibration completion-indicating output signal from said calibration completion-detecting circuit, a switching circuit having first, second and third switching elements between said memory circuit and each of said respired amount of air-indicating signal generator, reference level setting circuit and peak-to-peak amplitude detector respectively, and a switch control circuit for receiving an output signal from said flip-flop circuit to control said switching circuit.

7. A device according to claim 6, wherein said flip-flop circuit has first and second output terminals for generating a high level signal from the first output terminal before said flip-flop circuit receives said calibration completion-indicating signal and for generating a high level signal from the second output terminal after said flip-flop circuit receives said calibration completion-indicating signal; and said switch control circuit includes a clock pulse generator, an AND circuit having input terminals respectively connected to said clock generator and to said first output terminal of said flip-flop circuit, a first switch driving section for permitting in accordance with an output signal from said AND circuit, said first and second switching elements to operate in such a manner that when one of said first and second switching elements is closed, the other switching element is opened, and a second switch driving section connected to said second output terminal of said flip-flop circuit to operate said third switching element in accordance with an output signal from the second output terminal of said flip-flop circuit.

8. A device according to claim 7, which further comprises an inhalation phase detecting circuit for generating a pulse in an inhalation phase of a respiration signal from said impedance pneumograph, and wherein said switch control circuit includes an AND circuit having input terminals respectively connected to said second output terminal of said flip-flop circuit and to said inhalation phase detecting circuit and an output terminal connected to said second switch driving section.

9. A device according to claim 1, wherein said memory circuit includes an analog-digital converter for converting output signals from said respired amount of air-indicating signal generator, reference level setting circuit and peak-to-peak amplitude detector into digital signals, and a memory connected to receive at its input terminal a digital signal corresponding to said output signal from said respired amount of air-indicating signal generator and receive at its address terminal digital signals corresponding respectively to said output signals from said reference level setting circuit and peak-to-peak amplitude detector.

10. A device according to claim 9, wherein said memory circuit includes a memory element for storing therein, when said memory circuit is placed in a write-in mode, the largest address value of address values corresponding to said output signal from said reference level setting circuit, and a comparator for comparing, when said memory circuit is placed in a readout mode, an address value corresponding to said output signal from said peak-to-peak amplitude detector with said largest address value stored in said memory element and, where the former address value is larger than the latter largest address value, generating an output signal to render ineffective an output information read out from said memory by said former address value.

11. A device according to claim 1, wherein said respired amount of air-indicating signal generator includes means for generating a signal representing an inhaled amount of air; said reference level setting circuit includes means for drawing out only a signal corresponding to an inhalation phase of an output signal from said impedance pneumograph; said calibration completion detecting circuit produces an output signal when an inhaled amount of air-indicating signal from said respired amount of air-indicating signal generator has exceeded a specified level; and said operation mode selecting means sets said memory circuit to readout mode when receiving an output signal from said calibration completion-detecting circuit and causes said memory circuit to receive said output signal from said peak-to-peak amplitude detector as an address signal, thereby to provide an inhalated amount of air-indicating information signal corresponding to said address signal.

12. A device according to claim 11, which further comprises a display means for displaying output information read out from said memory circuit.

13. A device according to claim 11, wherein said respired amount of air-indicating signal generator includes a hot wire anemometer and an integrator circuit for integrating only an inhalation phase component of an output signal from said hot wire anemometer to supply an output signal to said calibration completion-detecting circuit.

14. A device according to claim 13, wherein said respired amount of air-indicating signal generator further includes a linearizer connected between said hot wire anemometer and said integrator circuit to generate an output signal linearly varying with respect to an amount of air respired by said body.

15. A device according to claim 13, wherein said calibration completion-detecting circuit includes a signal generator connected to said hot wire anemometer to generate a digital signal having high and low levels corresponding respectively to inhalation and exhalation phases of respiration signal from said hot wire anemometer, a level detector for detecting that the level of an output signal from said integrator circuit has exceeded a specified level, and a first logic circuit for receiving output signals from said level detector and said signal generator to generate a pulse upon rise of the output signal generated from said signal generator after said level of an output signal from said integrator circuit has exceeded said specified level.

16. A device according to claim 11, wherein said operation mode selecting means includes a flip-flop circuit for receiving said calibration completion-indicating output signal from said calibration completion-detecting circuit, a switching circuit having first, second and third switching elements between said memory circuit and each of said respired amount of air-indicating signal generator, reference level setting circuit and peak-to-peak amplitude detector respectively, and a switch control circuit for receiving an output signal from said flip-flop circuit to control said switching circuit.

17. A device according to claim 16, wherein said flip-flop circuit has first and second output terminals for generating a high level signal from the first output terminal before said flip-flop circuit receives said calibration completion-indicating signal and for generating a high level signal from the second output terminal after said flip-flop circuit receives said calibration completion-indicating signal; and said switch control circuit includes a clock generator, an AND circuit having input terminals respectively connected to said clock pulse generator and to said first output terminal of said flip-flop circuit, a first switch driving section for permitting, in accordance with an output signal from said AND circuit, said first and second switching elements to operate in such a manner that when one of said first and second switching elements is closed, the other switching element is opened, and a second switch driving section connected to said second output terminal of said flip-flop circuit to operate said third switching element in accordance with an output signal from the second output terminal of said flip-flop circuit.

18. A device according to claim 17, which further comprises an exhalation phase detecting circuit for generating a pulse in an exhalation phase of a respiration signal from said impedance pneumograph, and wherein said switch control circuit includes an AND circuit having input terminals respectively connected to said second output terminal of said flip-flop circuit and to said exhalation phase detecting circuit and an output terminal connected to said second switch driving section.

19. A device according to claim 11, wherein said memory circuit includes an analog-digital converter for converting output signals from said respired amount of air-indicating signal generator, reference level setting circuit and peak-to-peak amplitude detector into digital signals, and a memory connected to receive at its input terminal a digital signal corresponding to said output signal from said respired amount of air-indicating signal generator and receives at its address terminal digital signals corresponding respectively to said output signals from said reference level setting circuit and peak-to-peak amplitude detector.

20. A device according to claim 19, wherein said memory circuit includes a memory element for storing therein, when said memory circuit is placed in a write-in mode, the largest address value of address values corresponding to said output signal from said reference level setting circuit, and a comparator for comparing, when said memory circuit is placed in a readout mode, an address value corresponding to said output signal from said peak-to-peak amplitude detector when said largest address value stored in said memory element and, where the former address value is larger than the latter largest address value, generating an output signal to render ineffective an output information read out from said memory by said former address value.

* * * * *